US005691359A

United States Patent [19]

Fischer et al.

[11] Patent Number: 5,691,359
[45] Date of Patent: Nov. 25, 1997

[54] HETEROCYCLYLCARBONYL SUBSTITUTED BENZOFURANYL- AND -THIOPHENYL-ALKANECARBOXYCLIC ACID DERIVATIVES

[75] Inventors: Rüdiger Fischer, Köln; Gabriele Bräunlich; Mazen Es-Sayed, both of Wuppertal; Rudolf Hanko, Düsseldorf, all of Germany; Stephen Tudhope, Windsor, Great Britain; Graham Sturton, Bray, Great Britain; Trevor Abram, Marlow, Great Britain; Mary F. Fitzgerald, Begbroke, Great Britain

[73] Assignee: Bayer Aktiengesellschaft, Leverkusen, Germany

[21] Appl. No.: 447,661

[22] Filed: May 23, 1995

[30] Foreign Application Priority Data

May 31, 1994 [GB] United Kingdom ............... 9410877

[51] Int. Cl.⁶ .................. C07D 401/06; A61K 31/44
[52] U.S. Cl. ................. 514/337; 514/444; 514/365; 514/422; 546/284.1; 549/57; 549/60; 548/200; 548/525
[58] Field of Search .................. 546/268, 284.1; 514/337, 444; 549/60

[56] References Cited

U.S. PATENT DOCUMENTS 5,120,742  6/1992  Rasmusson et al. ............ 546/77

FOREIGN PATENT DOCUMENTS 0146243  6/1985  European Pat. Off. .
0551662  7/1993  European Pat. Off. .
0623607  11/1994  European Pat. Off. .

OTHER PUBLICATIONS

S. Nagata et al, Int. Arch. Allergy Immunol., vol. 97, pp. 194–199 (1992).

*Primary Examiner*—Jane Fan
*Attorney, Agent, or Firm*—Sprung Kramer Schaefer & Briscoe

[57] ABSTRACT

Heterocyclylcarbonyl substituted benzofuranyl- and thiophenyl-alkanecarboxylic acid derivatives are prepared by reacting appropriately substituted hydroxybenzene butanoic acid esters with heterocyclic ketones. The inventive compounds can be used for the preparation of medicaments, particularly of medicaments for the treatment and prevention of acute and chronic inflammatory processes.

9 Claims, No Drawings

HETEROCYCLYLCARBONYL SUBSTITUTED BENZOFURANYL- AND -THIOPHENYL-ALKANECARBOXYCLIC ACID DERIVATIVES

The invention relates to heterocyclylcarbonyl substituted benzofuran-alkanecarboxyclic acid derivatives, processes for their preparation and their use in medicaments.

It is known that the NADPH oxidase of phagocytes is the physiological source to the superoxide radical anion and reactive oxygen species derived therefrom which are important in the defence against pathogens. Uncontrolled formation leads to tissue damage in inflammatory processes. It is additionally known that elevation of phagocyte Cyclic AMP leads to inhibition of oxygen radical production and that this cell function is more sensitive than others such as aggregation or enzyme release (cf. Ink Arch. Allergy Immunol., vol. 97: pp 194–199, 1992).

Benzofuran- and benzothiophene derivatives having lipoxygenase-inhibiting action are described in the publication EP 146 243.

Surprisingly it was found that compounds given by the general formula (I) inhibited oxygen radical formation and elevated cellular cyclic AMP levels probably by inhibition of phagocyte phosphodiesterase activity.

The invention relates to heterocyclylcarbonyl substituted benzofuranyl- and thiophenyl-alkanecarboxyclic acids derivatives of the general formula (I)

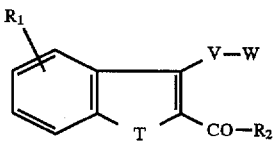

in which $R^1$ represents hydrogen, halogen, carboxyl, cyano, nitro, trifluoromethyl or a group of a formula $-OR^3$ or $-SR^4$, in which $R^3$ and $R^4$ are identical or different and denote cycloalkyl having 3 to 6 carbon atoms, hydrogen, a 5 to 7-membered saturated or unsaturated heterocycle having up to 4 heteroatoms from the series comprising N, S and/or O, which is optionally substituted by identical or different substituents from the series comprising halogen, cyano, nitro or by straight-chain or branched alkyl having up to 6 carbon atoms or denote straight-chain or branched alkyl or alkenyl each having up to 8 carbon atoms, and each of which is optionally monosubstituted to trisubstituted by identical or different substituents from the series comprising trifluoromethyl, halogen, cyano, carboxy, hydroxy, straight-chain or branched alkoxy, alkoxycarbonyl or acyl each having up to 6 carbon atoms or by a 5- to 7-membered saturated or unsaturated heterocycle having up to 4 heteroatoms from the series comprising N, S and O and to which an aromatic ting can be fused, or by phenyl, wherein all rings are optionally monosubstituted to trisubstituted by identical or different substituents from the series comprising nitro, halogen, carboxy or straight-chain or branched alkyl or alkoxycarbonyl each having up to 6 carbon atoms, or alkyl or alkenyl are substituted by a group of formula $-CO-NR^5R^6$ in which $R^5$ and $R^6$ are identical or different and denote phenyl, benzyl, hydrogen, formyl, straight-chain or branched alkyl or alkenyl each having up to 6 carbon atoms and which are optionally substituted by carboxy, hydroxy, straight-chain or branched alkoxycarbonyl having up to 6 carbon atoms, or $R^3$ denotes a hydroxyl protecting group, T represents an oxygen or sulfur atom V represents a straight-chain or branched alkylene or alkenylene chain each having 2 to 8 carbon atoms, W represents cyano, 1H-tetrazolyl or a group of a formula $-CO-R^7$, $-CO-NR^8R^9$, $-CONR^{10}-SO_2-R^{11}$ or $PO(OR^{12})(OR^{13})$, in which $R^7$ denotes hydroxyl, cycloalkyloxy having up 3 to 7 carbon atoms or straight-chain or branched alkoxy having up to 8 carbon atoms, $R^8$, $R^9$ and $R^{10}$ are identical or different and denote hydrogen, phenyl, benzyl, straight-chain or branched alkyl or acyl each having up to 6 carbon atoms and which are optionally substituted by hydroxyl, or $R^8$ and $R^9$ denote hydroxyl, $R^{11}$ denotes a straight-chain or branched alkyl having up to 6 carbon atoms, which is optionally substituted by phenyl or trifluoromethyl, or denotes phenyl, which is optionally substituted by substituents from the series comprising halogen, cyano, nitro or by straight-chain or branched alkyl having up to 6 carbon atoms, $R^{12}$ and $R^{13}$ are identical or different and represent hydrogen or straight-chain or branched alkyl having up to 6 carbon atoms, represents a 5 to 7 membered, saturated or unsaturated heterocycle, which can contain up to three oxygen, sulphur and/or nitrogen atoms as heteroatoms and to which further a benzene ring can be fused and wherein both rings are optionally monosubstituted to trisubstituted by identical or different substituents from the series comprising hydroxyl, halogen, nitro, 1H-tetrazolyl, trifluoromethyl, trifluoromethoxy, difluoromethyl, difluoromethoxy, cyano, carboxy, straight-chain or branched alkyl, alkoxy, alkoxycarbonyl or acyl each having up to 8 carbon atoms or by a group of formula $-NR^{14}R^{15}$, $-SR^{16}$, $SO_2R^{17}$ or $-O-SO_2R^{18}$, in which $R^{14}$ and $R^{15}$ have the first meaning shown above for $R^8$ and $R^9$ and are identical to the latter or different from the latter, $R^{16}$ denotes straight-chain or branched alkyl having up to 6 carbon atoms, $R^{17}$ and $R^{18}$ are identical or different and represent straight-chain or branched alkyl having up to 6 carbon atoms, benzyl or phenyl, which are optionally substituted by trifluoromethyl, halogen or straight-chain or branched alkyl having up to 6 carbon atoms, and salts thereof.

The heterocyclylcarbonyl substituted benzofuranyl- and thiophenyl-alkane-carboxylic acid derivatives according to the invention can also be present in the form of their salts. In general, salts with organic or inorganic bases or acids may be mentioned here.

Physiologically acceptable salts are preferred in the context of the present invention. Physiologically acceptable salts of the heterocyclylcarbonyl substituted benzofuranyl- and thiophenyl-alkanecarboxylic acid derivatives can be metal or ammonium salts of the substances according to the invention, which contain a free carboxylic group. Those which are particularly preferred are, for example, sodium, potassium, magnesium or calcium salts, and also ammonium salts which are derived from ammonia, or organic amines, such as, for example, ethylamine, di- or triethylamine, di- or triethanolamine, dicyclohexylamine, dimethylaminoethanol, arginine, lysine or ethylenediamine.

Physiologically acceptable salts can also be salts of the compounds according to the invention with inorganic or organic acids. Preferred salts here are those with inorganic acids such as, for example, hydrochloric acid, hydrobromic acid, phosphoric acid or sulphuric acid, or salts with organic carboxylic or sulphonic acids such as, for example, acetic acid, maleic acid, fumaric acid, malic acid, citric acid, tartaric acid, ethanesulphonic acid, benzenesulphonic acid, toluenesulphonic acid or naphthalenedisulphonic acid.

The compounds according to the invention can exist in stereoisomeric forms which either behave as image and mirror image (enantiomers), or which do not behave as image and mirror image (diastereomers). The invention relates both to the antipodes and to the racemate forms, as well as the diastereomer mixtures. The racemate forms, like the diastereomers, can be separated into the stereoisomerically uniform constituents in a known manner.

Hydroxyl protective group in the context of the abovementioned definition in general represents a protective group from the series comprising: trimethylsilyl, tert.butyldimethylsilyl, benzyl, 4-nitrobenzyl, 4-methoxybenzyl, acetyl, tetrahydropyranyl and benzoyl.

Heterocycle in general represents a 5- to 7-membered saturated or unsaturated, preferably 5- to 6- membered, saturated or unsaturated ring which can contain up to 4 oxygen, sulphur and/or nitrogen atoms as heteroatoms and to which further benzene ring can be fused.

The following are mentioned as preferred: thienyl, furyl, pyrrolyl, 1,2-thiazolyl, pyridyl, pyrimidyl, pyrazinyl, pyridazinyl, quinolyl, isoquinolyl, quinazolyl, quinoxazolyl, cinnolyl, thiazolyl benzothiaazolyl, isothiazolyl, benzisothiazolyl, oxazolyl, benzoxazolyl, isoxazolyl, imidazolyl, benzimidazolyl, benzo[b]-thiophenyl, indolyl, morpholinyl, pyrrolidinyl, piperidyl, piperazinyl, oxazolyl, oxazolinyl, triazolyl or tetrazolyl.

Preferred compounds of the general formula (I) are those in which $R^1$ represents hydrogen, fluorine, chlorine, bromine, nitro, trifluoromethyl or a group of a formula —$OR^3$ or —$SR^4$,
in which $R^3$ and $R^4$ are identical or different and denote hydrogen, cyclopropyl, cyclobutyl, cyclopentyl, cyclohexyl, chinolyl, pyridyl, imidazolyl, 1,3-thiazolyl or thienyl, which are optionally substituted by identical or different substituents from the series comprising fluorine, chlorine, bromine, iodine, cyano, nitro or by straight-chain or branched alkyl having up to 5 carbon atoms or denote straight-chain or branched alkyl or alkenyl each having up to 6 carbon atoms, and each of which is optionally monosubstituted to trisubstituted by identical or different substituents from the series comprising trifluoromethyl, fluorine, chlorine, bromine, iodine, cyano, carboxy, hydroxy, straight-chain or branched alkoxy, alkoxycarbonyl or acyl each having up to 5 carbon atoms or by chinolyl, pyridyl, pyrazolyl, 1,3-thiadiazolyl, thienyl, imidazolyl or N-methyl-substituted imidazolyl and to which benzene can be fused, or by phenyl, where in all rings are optionally monosubstituted to disubstituted by identical or different substituents from the series comprising nitro, fluorine, chlorine, bromine, iodine, carboxy or straight-chain or branched alkyl or alkoxycarbonyl each having up to 5 carbon atoms, or alkyl or alkenyl are substituted by a group of formula —CO—$NR^5R^6$
in which $R^5$ and $R^6$ are identical or different and denote phenyl, benzyl, hydrogen, formyl, straight-chain or branched alkyl or alkenyl each having up to 5 carbon atoms, which are optionally substituted by carboxy, hydroxy or straight-chain or branched alkoxycarbonyl having up to 4 carbon atoms,
or $R^3$ denotes acetyl, benzyl or tetrahydrofuranyl, T represents an oxygen or sulfur atom V represents a straight-chain or branched alkylene or alkenyl chain each having 2 to 6 carbon atoms, W represents cyano, 1H-tetrazolyl or a group of a formula —CO—$R^7$, —CO—$NR^8R^9$, —$CONR^{10}$—$SO_2$—$R^{11}$ or PO($OR^{12}$)($OR^{13}$),
in which $R^7$ denotes hydroxyl, cyclopropyloxy, cyclopentyloxy, cyclohexyloxy or straight-chain or branched alkoxy having up to 6 carbon atoms, $R^8$, $R^9$ and $R^{10}$ are identical or different and denote hydrogen, benzyl, phenyl, straight-chain or branched alkyl or acyl each having up to 4 carbon atoms and which are optionally substituted by hydroxyl,
or $R^8$ or $R^9$ denote hydroxyl, $R^{11}$ denotes straight-chain or branched alkyl having up to 5 carbon atoms, which is optionally substituted by phenyl or trifluoromethyl, or denotes phenyl, which is optionally substituted by substituents from the series comprising fluorine, chlorine, bromine, iodine, cyano, nitro or by straight-chain or branched alkyl having up to 4 carbon atoms, $R^{12}$ and $R^{13}$ are identical or different and represents hydrogen or straight-chain or branched alkyl having up to 6 carbon atoms, $R^2$ represents pyridyl, pyrryl, imidazolyl, pyrazolyl, thienyl, isothiazolyl, 1,3-thiazolyl or benzo[b]thiophenyl, wherein both rings are optionally monosubstituted to trisubstituted by identical or different substituents from the series comprising hydroxyl, fluorine, chlorine, bromine, iodine, nitro, tetrazolyl, trifluoromethyl, trifluoromethoxy, difluoromethyl, difluoromethoxy, cyano, carboxy, straight-chain or branched alkyl, alkoxy, alkoxycarbonyl or acyl each having up to 6 carbon atoms or by a group of formula —$NR^{14}R^{15}$, —$SR^{16}$, —$SO_2R^{17}$ or —O—$SO_2R^{18}$,
in which $R^{14}$ and $R^{15}$ have the first meaning shown above for $R^8$ and $R^9$ and are identical to the latter or different from the latter, $R^{16}$ denotes straight-chain or branched alkyl having up to 4 carbon atoms, $R^{17}$ and $R^{18}$ are identical or different and represent straight-chain or branched alkyl having up to 5 carbon atoms or phenyl, which is optionally substituted by trifluoromethyl, fluorine, chlorine, bromine or straight-chain or branched alkyl having up to 3 carbon atoms, and salts thereof.

Particularly preferred compounds of the general formula (I) are those
in which $R^1$ represents hydrogen, fluorine, chlorine, bromine, nitro, trifluoromethyl or a group of a formula —$OR^3$ or —$SR^4$,
in which $R^3$ denotes hydrogen, tetrahydropyranyl, benzyl, acetyl, cyclopropyl, cyclobutyl, cyclopentyl, cyclohexyl, chinolyl, pyridyl, imidazolyl or thienyl, which are optionally substituted by identical or different substituents from the series comprising fluorine, chlorine, bromine, cyano, nitro or by straight-chain or branched alkyl having up to 4 carbon atoms or denotes straight-chain or branched alkyl or alkenyl each having up to 5 carbon atoms, and each of which is optionally monosubstituted to disubstituted by identical or different sustituents from the series comprising trifluoromethyl, fluorine, chlorine, bromine, cyano, carboxy, hydroxy, straight-chain or branched alkoxy, alkoxycarbonyl or acyl each having up to 4 carbon atoms or by chinolyl, pyridyl, imidazolyl or N-methyl-substituted imidazolyl and to which benzene can be fused, or by phenyl, wherein all rings are optionally monosubstituted to di-substituted by identical or different substituents from the series comprising nitro, fluorine, chlorine, bromine, carboxy or straight-chain or branched alkyl, alkoxycarbonyl each having up to 4 carbon atoms, or alkyl or alkenyl are substituted by a group of formula —CO—NR$^5$R$^6$ in which R$^5$ and R$^6$ are identical or different and denote phenyl, benzyl, hydrogen, formyl, straight-chain or branched alkyl each having up to 4 carbon atoms, which are optionally substituted by carboxy, hydroxy or straight-chain or branched alkoxycarbonyl having up to 3 carbon atoms.

R$^4$ denotes straight-chain or branched alkyl having up to 4 carbon atoms,

T represents an oxygen atom or sulphur

V represents a straight-chain or branched alkylene or alkenylene chain having 2 to 5 carbon atoms, W represents cyano, 1H-tetrazolyl or a group of a formula —CO—R$^7$ or —CO—NR$^8$R$^9$, in which R$^7$ denotes hydroxyl, cyclopropyloxy, cyclopentyloxy, cyclohexyloxy or straight-chain or branched alkoxy having up to 5 carbon atoms, R$^8$ and R$^9$ are identical or different and denote phenyl, benzyl, hydrogen, straight-chain or branched alkyl or acyl each having up to 4 carbon atoms, and R$^2$ represents pyridyl, pyrryl, furyl, thienyl, 1,3-thiazolyl or benzo[b]thiophenyl, which are optionally monosubstituted to trisubstituted by identical or different substituents from the series comprising, hydroxyl, fluorine, chlorine, bromine, nitro, tetrazolyl, trifluoromethyl, trifluoromethoxy, difluoromethyl, difluoromethoxy, cyano, carboxy, straight-chain or branched alkyl, alkoxy, alkoxycarbonyl or acyl each having up to 5 carbon atoms or by a group of formula —NR$^{14}$R$^{15}$, SR$^{16}$ or —SO$_2$R$^{17}$, in which R$^{14}$ and R$^{15}$ have the meaning of R$^8$ and R$^9$, R$^{16}$ denotes straight-chain or branched alkyl having up to 3 carbon atoms, R$^{17}$ denotes straight-chain or branched alkyl having up to 3 carbon atoms or phenyl, and salts thereof.

A process for the preparation of the compounds of the general formula (I) has additionally been found, characterised in that compounds of the general formula (II)

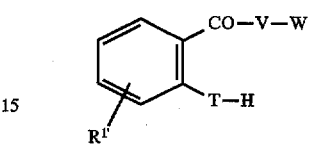

in which

T, V and W have the abovementioned meaning, and

R$^{1'}$ represents a group of formula —OR$^{3'}$, in which

R$^{3'}$ has the abovementioned meaning of R$^3$, but does not represent hydrogen, are reacted with compounds of the general formula (III)

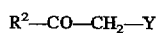

in which

R$^2$ has the abovementioned meaning and

Y represents a typical leaving group such as, for example, chlorine, bromine, iodine, tosylate or mesylate, preferably bromine, in inert solvents and in the presence of a base and, then, if appropriate, the protective groups are split off, the esters are hydrolysed, the acids are esterified with the appropriate alcohols in the presence of a catalyst or the compounds are alkylated or the esters are directly reacted with amines or the free carboxylic acids, if appropriate in the presence of above and/or an auxiliary, an amidation or sulfonamidation follows.

The process according to the invention can be illustrated by way of example by the following equations:

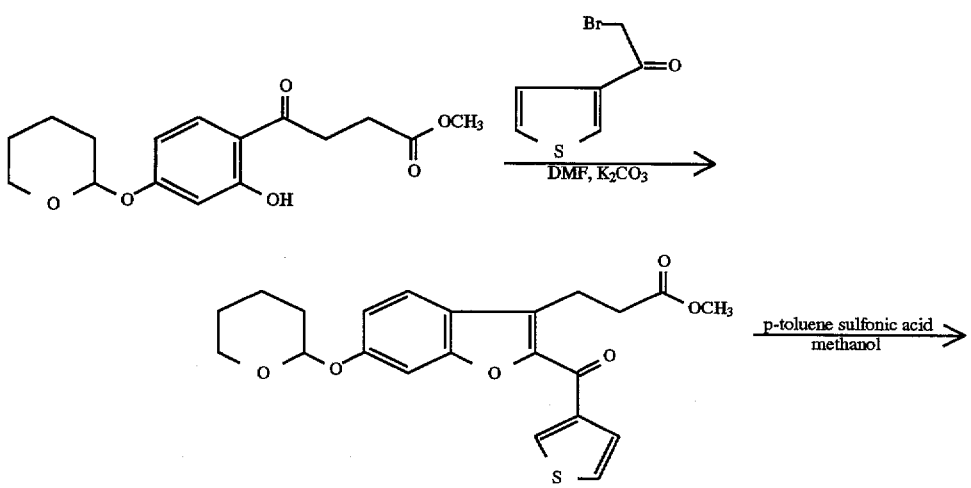

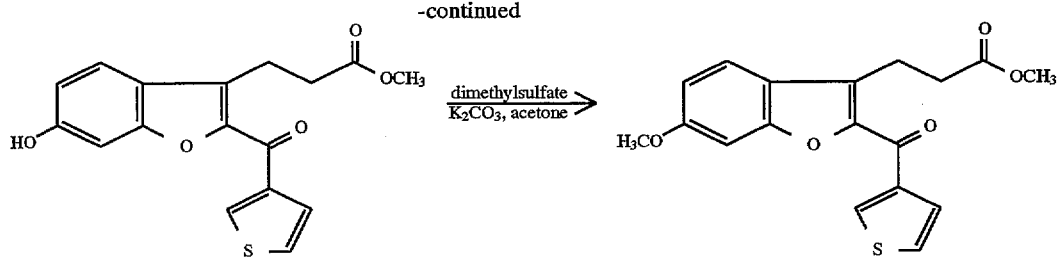

Suitable solvents are generally customary organic solvents which do not change under the reaction conditions. These include ethers such as diethyl ether, dioxane or tetrahydrofurane, acetone, dimethylsulfoxide, dimethylformamide or alcohols such as methanol, ethanol, propanol or halogenohydrocarbons such as dichlormethane, trichloromethane or tetrachloromethane. Dimethylformamide and dichloromethane are preferred.

Suitable bases are generally inorganic or organic bases. These preferably include alkali metal hydroxides such as, for example, sodium hydroxide, sodium hydrogencarbonate or potassium hydroxide, alkaline earth metal hydroxides such as, for example, barium hydroxide, alkali metal carbonates such as sodium carbonate, potassium carbonate, alkaline earth metal carbonates such as calcium carbonate, or alkaline metal oder alkaline earth metal alkoxides such as sodium methoxide or potassium methoxide, sodium ethoxide or potassium ethoxide or potassium tert.butoxide, or organic amines (trialkyl($C_1$–$C_6$)amines) such as triethylamine, or heterocycles such as 1,4-diazabicyclo[2.2.2]octane (DABCO), 1,8-diazabicyclo-[5.4.0]undec-7-ene (DBU), or amides such as sodium amides, lithium butyl amide or butyllithium, pyridine or methylpiperidine. It is also possible to employ alkali metals, such as sodium or its hydrides such as sodium hydride, as bases. Potassium carbonate, triethylamine, sodium hydrogencarbonate and sodium-hydroxide are preferred.

The process is in general carried out in a temperature range from +10° C. to 150° C., preferably from +20° C. to +60° C.

The process is generally carded out at normal pressure. However, it is also possible to carry out it at elevated pressure or at reduced pressure (for example in a range from 0.5 to 5 bar).

The base is employed in an amount from 1 mol to 10 mol, preferably from 1.0 mol to 2.1 mol, relative to 1 mol of the compounds of the general formula (III).

The compounds of the general formula (II), (III) (IV) and (V) are known or can be prepared by published methods.

The compounds according to the invention specifically inhibit the production of superoxide by polymorphonuclear leucocytes (PMN) without impairing other cell functions such as degranulation or aggregation. The inhibition was mediated by the elevation of cellular cAMP probably due to inhibition of the type IV phosphodiesterase responsible for its degradation They can therefore be employed in medicaments for controlling acute and chronic inflammatory processes.

The compounds according to the invention are preferably suitable for the treatment and prevention of acute and chronic inflammations of the airways, such as emphysema, alveolitis, shock lung, asthma, bronchitis, arteriosclerosis, arthrosis, inflammations of the gastro-intestinal tract and myocarditis. The compounds according to the invention are additionally suitable for reducing the damage to infarct tissue after reoxygenation. In this case the simultaneous administration of allopurinol to inhibit xanthine oxidase is of advantage. Combination therapy with superoxide dismutase is also of use.

Test Description

1. Preparation of human PMN

Blood was taken from healthy subjects by venous puncture and neutrophils were purified by dextran sedimentation and resuspended in the buffered medium.

2. Inhibition of FMLP-stimulated production of superoxide racidal anions.

Neutrophils ($2.5 \times 10^5$ ml$^{-1}$) were mixed with cytochrome C (1.2 mg/ml) in the wells of a microtitre plate. Compounds according to the invention were added in dimethyl sulphoxide (DMSO). Compound concentration ranged from 2.5 nM to 10 µM, the DMSO concentration was 0.1% v/v in all wells. After addition of cytochalasin b (5 µg×ml$^{-1}$) the plate was incubated for 5 min at 37° C. Neutrophils were then stimulated by addition of $4 \times 10^{-8}$ M FMLP and superoxide generation measured as superoxide dismutase inhibitable reduction of cytochrome C by monitoring the $OD_{550}$ in a Thermomax microtitre plate spectrophotometer. Initial rates were calculated using a Softmax kinetic calculation programme. Blank wells contained 200 units of superoxide dismutase.

The inhibition of superoxide production was calculated as follows:

$$\frac{[1-((Rx-Rb))]}{((Ro-Rb))} \cdot 100$$

Rx=Rate of the well containing the compound according to the invention.

Ro=Rate in the control well.

Rb=Rate in the superoxide dismutase containing blank well.

3. Measurement of PMN cyclic AMP concentration

The compounds according to the invention were incubated with $3.7 \times 10^6$ PMN for 5 min at 37° C. before addition of $4 \times 10^{-8}$ M FMLP. After 6 min protein was precipitated by the addition of 1% v/v conc. HCl in 96% v/v ethanol containing 0.1 mM EDTA. After centrifugation the ethanolic extracts were evaporated to dryness under $N_2$ and resuspended in 50 mM Tris/HCl pH 7.4 containing 4 mM EDTA. The cyclic AMP concentration in the extracts was determined using a cyclic AMP binding protein assay supplied by

9

Amersham International plc. Cyclic AMP concentrations were expressed as percentage of vehicle containing control incubations.

4. Assay of PMN phosphodiesterase

PMN suspensions ($10^7$ cells/ml) were sonicated for 6×10 sec on ice. Aliquots (100 µl) were incubated for 5 min at 37° C. with the compounds according to the invention or vehicle before the addition of $^3$H-cAMP (1 mM and 200 nCi per incubation). After 20 min the reaction was stopped by heating at 100° C. for 45 seconds. After cooling 100 mg of 5'-nucleotidase was added to each tube and the samples incubated for 15 min at 37° C. The conversion to $^3$H-adenosine was determined by ion-exchange chromatography on Dowex AG-1x (chloride form) followed by liquid scintillation counting. Percentage inhibition was determined by comparison to vehicle containing controls.

5. Effect of intravenously administered compounds on the FMLP-induced skin oedema guinea pigs Guinea pigs (600–800) were anaesthetized with pentobarbitone sodium (40 mg/kg, i.p.) and injected (i.v.) with a 0.5 ml mixture of pentamine sky blue (5% W/V) and $^{125}$I-HSA (1 uli/animal). 10 minutes later 3 intradermal injections of FMLP (10 µg/site), 1 injection of histamine (1 µg/site) and 1 injection of vehicle (100 µl of 0.2% DMSO V/V in Hanks Buffered salt solution) were made on the left hand side of the animal (preinjection sites). 5 minutes later the drug (1 ml/kg) or the vehicle (50% PEG 400 V/V in distilled water, 1 mg/kg) was administered (i.v.). 10 minutes later an identical pattern of interadermal injections was made on the opposite flank of the animal (post-injection sites). These responses were allowed to develop for 15 minutes before the animal was sacrificed and a blood sample taken.

Skin sites and plasma samples were counted for 1 minute on a gamma counter an the degree of oedema calculated as µl plasma/skin site. Statistical analysis was done by a paired t-test on the mean of the 3 preinjection site values of µl plasma obtained for FMLP/animal. The percentage inhibition of drug or vehicle was calculated as follow $$X\% = 1 - \frac{\overline{X} \, \mu l \text{ plasma (post-injection site)}}{\overline{X} \, \mu l \text{ plasma (pre-injection site)}} \times 100$$

6. Effect of orally administered compounds on the FMLP-induced skin oedema of guinea-pigs
in vivo Test's p.o.

Guinea-pigs (600–800 g) were fasted overnight and orally treated with vehide (1% Tylose w/v at 5 ml/kg) or drug (10 mg/kg; 2 mg/ml in 1% Tylose at 5 ml/kg) 40 minutes later the animals were anaestized with pentobarbitone sodium (40 mg/kg, i.P.) and 0.6 ml of a mixture of pontamine sky blue (5% w/v) and $^{125}$I-HSA (1 µci/animal) was injected (i.v.). 90 minutes after oral pretreatment FMLP (50 µg/site) was injected (i.d.) at 4 different sites, histamine (1 µg/site) and vehicle (100 µl, 1% DMSO v/v in Hanks buffered salt solution) were both injected (i.d.) at 2 different sites.

The responses were allowed to develop for 30 minutes before the animal was sacrificed and a blood sample taken. Skin sites and plasma samples were counted for 1 minute on a gamma counter. The degree of oedema was calculated as µl plasma/skin site. Statistical analysis was carried out by a Mann-Whitney U-test on the mean of the 4 values of µl Plasma obtained for FMLP/animal.

10

The new active compounds can be converted in a known manner into the customary formulations, such as tablets, coated tablets, pills, granules, aerosols, syrups, emulsions, suspensions and solutions, using inert, nontoxic, pharmaceutically suitable excipients or solvents. In this connection, the therapeutically active compound should in each case be present in a concentration of about 0.5 to 90% by weight of the total mixture, i.e. in amounts which are sufficient in order to achieve the dosage range indicated.

The formulations are prepared, for example, by extending the active compounds with solvents and/or excipients, if appropriate using emulsifiers and/or dispersants, where, for example, in the case of the use of water as a diluent, organic solvents can be used as auxiliary solvents if appropriate.

Administration is carried out in a customary manner, preferably orally or parenterally, in particular perlingually or intravenously.

In the case of parenteral administration, solutions of the active compound can be employed using suitable liquid vehicles.

In general, it has proved advantageous on intravenous administration to administer mounts from about 0.001 to 10 mg/kg, preferably about 0.01 to 5 mg/kg of body weight to achieve effective results, and on oral administration the dosage is about 0.01 to 25 mg/kg, preferably 0.1 to 10 mg/kg of body weight.

In spite of this, it may be necessary to depart from the mounts mentioned, in particular depending on the body weight or the type of application route, on individual behaviour towards the medicament, the manner of its formulation and the time or interval at which administration takes place. Thus, in some cases it may be sufficient to manage with less than the abovementioned minimum mount, while in other cases the upper limit mentioned must be exceeded. In the case of administration of relatively large amounts, it is advisable to divide these into several individual doses over the course of the day.

Solvents
I petrolether:ethylacetate 1:1
II petrolether:ethylacetate 5:1
III petrolether:ethylacetate 5:2
IV dichlormethane:methanol 95:5
V dichlormethane:methanol 9:1
VI dichlormethane
DMF dimethylformamide Starting compounds

EXAMPLE I

2'-Hydroxy-3-oxo-4'-[tetrahydro-2H-pyran-2-yl)oxy] benzenebutanoic acid methylester

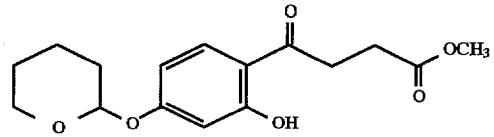

20.0 g (0.089 mol) 2',4'-Dihydroxy-3-oxo-benzenebutanoic acid methylester were dissolved in 200 ml dichloromethane/tetrahydrofuran (95:5) and 9.2 ml (0.1 mol) 3,4-dihydro-2H-pyran and 10 mg p-toluenesulfonic acid were added successively. The suspension was stirred at room temperature for 1 hour. 400 ml of a NaHCO$_3$ solution were added, the organic layer separated and washed three times with water. The organic phase was dried using Na$_2$SO$_4$

PREPARATION EXAMPLES

EXAMPLE 1

6-[(Tetrahydro-2H-pyran-2-yl)oxy]-2-(3-thienylcarbonyl)-3-benzofuran acid methylester

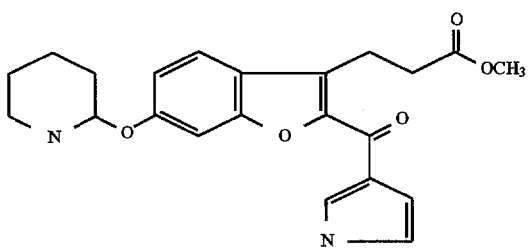

Equivalent amounts, 1.5 g (4.9 mmol) of 2'-Hydroxy-3-oxo-4'-[(tetrahydro-2H-pyran-2-yl)oxy]benzenebutanoic acid, methylester and 1.0 g (4.9 mmol) of 2-bromo-1-(3-thienyl)ethanone were dissolved in 50 ml acetone and 1,35 g (9.7 mol) of potassium carbonate were added. The suspension was heated under reflux for 16 hours. The mixture was filtered, the solvent was distilled off in vacuo and the residue was taken up in ethylacetate. The organic phase was washed three times with water, one time with a NaCl solution, dried over Na$_2$SO$_4$ and concentrated in vacuo. The residue was further purified by chromatography (silica gel 60). Yield: 0.83 g (41%) R$_f$=0.43, II

EXAMPLE 2

6-Hydroxy-2-(3-thienylcarbonyl)-3-benzofuranpropanoic acid methylester

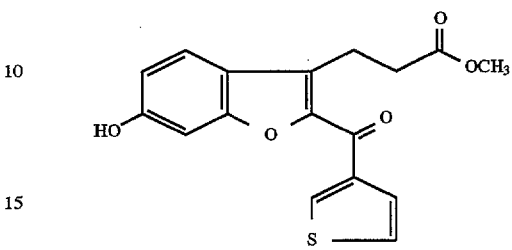

0.7 g (1.7 mmol) of 6-[(tetrahydro-2H-pyran-1-yl)oxy]-2-(3-thienylcarbonyl)-3-benzofuranpropanoic acid methylester were dissolved in 30 ml methanol and 5 mg p-toluenesulfonic acid were added. The suspension was stirred at r.t. for 2 hours. The solvent was distilled off, the residue solved in ethylacetate and washed two times with water, once with a Na$_2$HCO$_3$ solution and once with a NaCl solution. The organic layer was dried using Na$_2$SO$_4$, concentrated in vacuo and the residue was further purified by chromatography (silica gel 60). Yield: 0.4 g (72%) R$_f$=0.25, II The compounds shown in Table 1 were prepared in analogy to the procedure of Example 2:

TABLE 1

| Example No. | R$^1$ | R$^2$ | R$_f$ | Yield (% of theory) |
|---|---|---|---|---|
| 3 | —OH | (benzothiophene) | 0.55(III) | 70 |
| 4 | —OH | (2-pyridyl) | 0.34 (I) | 71.1 |
| 5 | —OH | (3-pyridyl) | 0.26 (I) | 91.2 |
| 6 | —OH | (4-pyridyl) | 0.18 (I) | 84.4 |

TABLE 1-continued
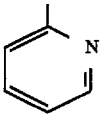
| Example No. | R¹ | R² | $R_f$ | Yield (% of theory) |
|---|---|---|---|---|
| 7 | —OCH₂—CO₂CH₃ | 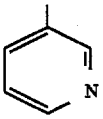 | 0.39 (I) | 78 |
| 8 | —O—CH₂—CO—OCH₃ |  | 0.34 (I) | 47.2 |
| 9 | —O—CH—CONH₂ |  | 0.15 (I) | 59.3 |
| 10 | —O—CH₂—CONH₂ |  | 0.13 (I) | 55.4 |
| 11 | —O—CH₂—CONH₂ | 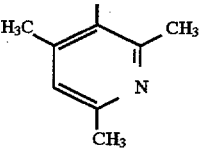 | 0.41 (V) | 76.2 |
| 12 | —OH | 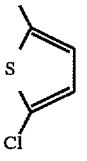 | 0.45 (V) | 94.1 |
| 13 | —OH | 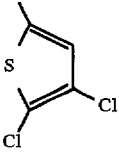 | 0.35 (III) | 74.6 |
| 14 | —OH | 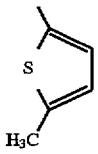 | 0.30 (III) | 86.9 |
| 15 | —OH | 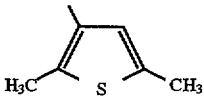 | 0.25 (III) | 83.0 |
| 16 | —OH |  | 0.32 (III) | 85.7 |

TABLE 1-continued

[Structure: benzofuran with R₁ on benzene ring, (CH₂)₂CO₂CH₃ at 3-position, and C(=O)R₂ at 2-position]

| Example No. | R¹ | R² | $R_f$ | Yield (% of theory) |
|---|---|---|---|---|
| 17 | —O—CH₂—CO—OCH₃ | 2,4,6-trimethylpyridin-3-yl (H₃C, CH₃, CH₃ substituents) | 0.63 (V) | 94.4 |
| 18 | —O—CH₂—CONH₂ | 2,4,6-trimethylpyridin-3-yl (H₃C, CH₃, CH₃ substituents) | 0.35 (V) | 98.9 |
| 19 | —O—CH₂—CO—OCH₃ | 5-chlorothien-2-yl | 0.34 (III) | 87.0 |
| 20 | —O—CH₂—CONH₂ | 5-chlorothien-2-yl | 0.55 (V) | 91.6 |
| 21 | —O—CH₂—CO—OCH₃ | 4,5-dichlorothien-2-yl | 0.41 (III) | 71.4 |
| 22 | —O—CH₂—CONH₂ | 4,5-dichlorothien-2-yl | 0.58 (V) | 98.2 |
| 23 | —O—CH₂—CO—OCH₃ | 4-methylthien-2-yl | 0.45 (III) | 93.6 |
| 24 | —O—CH₂—CONH₂ | 5-methylthien-2-yl | 0.62 (V) | 90.9 |

TABLE 1-continued
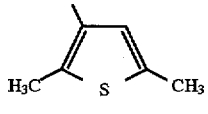
| Example No. | $R^1$ | $R^2$ | $R_f$ | Yield (% of theory) |
|---|---|---|---|---|
| 25 | —O—CH$_2$—CO—OCH$_3$ | 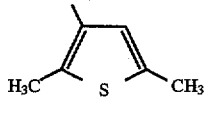 | 0.38(III) | 89.4 |
| 26 | —O—CH$_2$—CONH$_2$ | 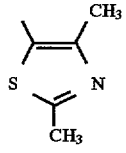 | 0.60 (V) | 98.7 |
| 27 | —O—CH$_2$—CO—OCH$_3$ | 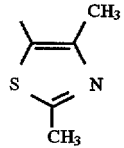 | 0.55(III) | 86.4 |
| 28 | —O—CH$_2$—CONH$_2$ | 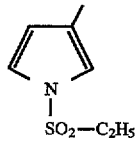 | 0.11(III) | quant. |
| 29 | —OH | 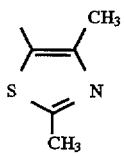 | 0.08 (II) | quant. |
| 30 | —OH | 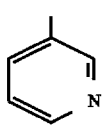 | 0.47(III) | 98.2 |
| 31 | —Cl | 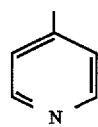 | 0.56(III) | 16.4 |
| 32 | —Cl | 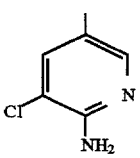 | 0.58(III) | 7.8 |
| 33 | —OH |  | 0.34 (I) | 70 |

EXAMPLE 34

6-hydroxy-2-(4-pyridyl-)-3-benzofuran-propanoic acid

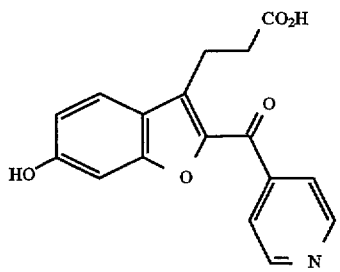

1.5 g (4.6 mmol) of the compound from starting compounds Example III were dissolved in 50 ml methanol/tetrahydrofuran (1:1) and 5.5 ml of a 2 NaOH solution were added. The mixture was stirred at room temperature for 24 hours, dissolved in water and acidified with 1N hydrochloric acid. The precipitate was filtered off, washed several times with water and dried in vacuo. The further reaction was carded out as described in Example 1. Yield: 1,25 g (87%) $R_f$: 0.01 (IV)

We claim:

1. A heterocyclylcarbonyl substituted benzofuranyl-alkanecarboxylic acid derivative of the formula

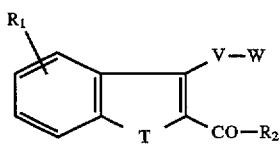

wherein $R^1$ represents chlorine or a group of a formula —$OR^3$ in which $R^3$ denotes hydrogen, tetrahydropyranyl, acetyl or denotes straight-chain or branched alkyl or alkenyl each having up to 8 carbon atoms, and each of which is substituted by alkoxycarbonyl having up to 6 carbon atoms, or alkyl is substituted by a group of formula —CO—$NH_2$ V represents alkylene having 2 to 8 carbon atoms, W represents a group of formula —CO—$R^7$ in which $R^7$ denotes hydroxyl or straight-chain or branched alkoxy having up to 8 carbon atoms, and $R^2$ represents pyridyl, thienyl, 1,3-thiazolyl or benzo[b]thiophenyl, which are optionally monosubstituted to trisubstituted by identical or different substituents from the group consisting of halogen, alkyl having up to 8 carbon atoms, $NH_2$ or $SO_2$—$C_6H_5$.

or a salt thereof.

2. A heterocyclylcarbonyl substituted benzofuranyl-alkanecarboxylic acid derivative according to claim 1, wherein $R^1$ represents chlorine or a group of the formula —$OR^3$ in which $R^3$ denotes hydrogen, tetrahydropyranyl, or acetyl or denotes a straight-chain or branched alkyl or alkenyl each having up to 5 carbon atoms which is substituted by alkoxycarbonyl having up to 4 carbon atoms, or is alkyl which is substituted by a group of the formula —$CONH_2$, V represents —$(CH_2)_2$—

W represents a group of the formula —$COR^7$ in which $R^7$ denotes hydroxyl or straight-chain or branched alkoxy having up to 5 carbon atoms and $R^2$ represents pyridyl, thienyl, 1,3-thiazolyl or benzo[b]thiophenyl, which are optionally monosubstituted to trisubstituted by identical substituents from the group consisting of chlorine, alkyl having up to 5 carbon atoms, $NH_2$ or $SO_2$—$C_6H_5$ or a salt thereof.

3. A heterocyclylcarbonyl substituted benzofuran-alkane carboxylic acid according to claim 1, wherein such compound is 6-[tetrahydro-2H-pyran-2yl)oxy]-2-(3-thienylcarbonyl)-3-benzofuranpropanoic acid methylester of the formula

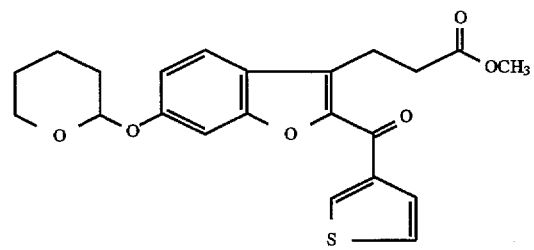

or a salt thereof.

4. A heterocyclylcarbonyl substituted benzofuran-alkane carboxylic acid according to claim 1, wherein such compound is 6-hydroxy-2-(3-thienylcarbonyl)-3-benzofuranpropanoic acid methylester of the formula

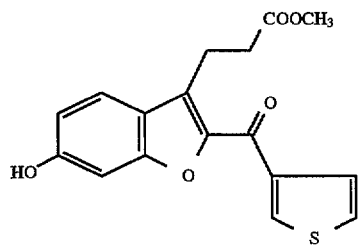

or a salt thereof.

5. A heterocyclylcarbonyl substituted benzofuran-alkane carboxylic acid according to claim 1, wherein such compound is 6-hydroxy-2-(4-pyridylcarbonyl)3-benzofuranpropanoic acid methylester of the formula or a salt thereof.

6. A heterocyclylcarbonyl substituted benzofuran-alkane carboxylic acid according to claim 1, wherein such compound is 6-hydroxy-2-(3-pyridylcarbonyl)-3-benzofuranpropanoic acid methylester of the formula

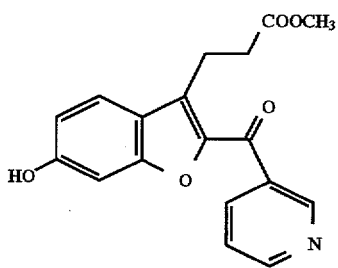

or a salt thereof.

7. A heterocyclylcarbonyl substituted benzofuran-alkane carboxylic acid according to claim 1, wherein such compound is 6-hydroxy-2-(4-pyridylcarbonyl)-3-benzofuran propanoic acid of the formula

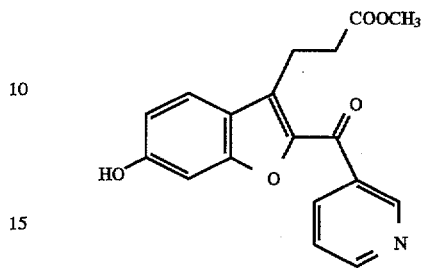

or salt thereof.

8. A composition for the treatment of acute and chronic inflammatory processes comprising an mount effective therefor of a compound or salt thereof according to claim 1 and a pharmacologically acceptable diluent.

9. A method of treating acute and chronic inflammation of the airways of the lungs by inhibiting the production of superoxide by PMN and increasing cAMP levels which comprises administering to a patient in need thereof an effective amount of a compound according to claim 1.

* * * * *